United States Patent [19]

Christinger

[11] 4,295,477

[45] Oct. 20, 1981

[54] MULTIPLE SAMPLING DEVICE HAVING MOLDED VALVE AND HUB

[75] Inventor: Werner Christinger, Franklin Lakes, N.J.

[73] Assignee: Becton, Dickinson and Company, Paramus, N.J.

[21] Appl. No.: 66,818

[22] Filed: Aug. 15, 1979

[51] Int. Cl.³ .............................................. A61B 5/14
[52] U.S. Cl. .................................... 128/766; 128/764
[58] Field of Search .............. 128/766, 764, 763, 274, 128/276, 218 NV, 350 V

[56] References Cited

U.S. PATENT DOCUMENTS

| | | | |
|---|---|---|---|
| 3,469,572 | 9/1969 | Nehring | 128/766 X |
| 3,817,240 | 6/1974 | Ayres | 128/766 |
| 3,848,579 | 11/1974 | Villa-Real | 128/766 |
| 4,106,497 | 8/1978 | Percarpio | 128/766 |
| 4,134,512 | 1/1979 | Nugent | 128/764 X |
| 4,212,308 | 7/1980 | Percarpio | 128/766 |

FOREIGN PATENT DOCUMENTS 2349996  2/1974  Fed. Rep. of Germany ...... 128/766

*Primary Examiner*—Kyle L. Howell

[57] ABSTRACT

A multiple blood sampling device includes a housing having a chamber therein, a first cannula attached to one end of the housing, a second cannula attached to the other end of the housing, and a one-way valve provided within the housing. Part of the housing is molded around a portion of the valve to securely hold it in place. Another portion of the valve extends into the chamber where it provides valving action in response to the relative pressures in to two cannulas. When one cannula penetrates the blood vessel of a patient and the other punctures the stopper of an evacuated tube, blood is able to flow through the device and into the tube. Backflow is prevented by the one-way valve.

5 Claims, 5 Drawing Figures

MULTIPLE SAMPLING DEVICE HAVING MOLDED VALVE AND HUB

BACKGROUND OF THE INVENTION

The field of the invention relates to multiple sampling devices for obtaining blood samples from a patient.

Multiple sampling devices have been used to advantage where one wishes to take a plurality of blood samples from a patient without risk of either backflow or spillage. Such devices often include a plastic needle hub having a chamber therein, an intravenous cannula attached to one end of the hub, a second cannula attached to the other end of the hub, and a one-way elastomeric valve positioned within the chamber. Two particularly advantageous assemblies are described in commonly assigned Ser. Nos. 915,670 and 915,671, both filed June 15, 1978. U.S. Pat. Nos. 3,817,240 and 3,874,367 are further examples of needle assemblies which are now known to the art.

According to present techniques for manufacturing needle assemblies, first and second polymeric hub assemblies are molded. An elastomeric valve is positioned upon receiving means on one hub, and the two hubs may thereafter be joined by conventional methods. Cannulas may be secured to the respective hub assemblies so that a fluid may flow from one cannula, through the valve within the hub assembly, and out through the other cannula. Epoxy may be used for attaching the cannulas to the hub assemblies either before or after they are joined.

SUMMARY OF THE INVENTION

In order to provide an inexpensive and extremely reliable multiple sampling apparatus, the valve and hub are molded in a two-material molding machine such that at least a portion of the valve is encased by a hub portion. The position of the valve is accordingly fixed with respect to the hub so that malfunction due to dislodgement is practically impossible. After pre-assembly of the cannulas into respective first and second hub assemblies, the two halves are joined together permanently.

According to one embodiment of the invention, a sleeve valve is utilized for preventing backflow to the patient through the intravenous cannula. The valve has a bore therein for accomodating the distal end of the intravenous cannula. It also includes an enlarged portion surrounded by the hub which effectively holds it in place. The cannula is slotted near its distal end and the slot is covered by the sleeve portion of the valve. When suction is applied through the use of an evacuated tube, the valve opens to allow blood to pass through the slot and into the tube. Should back pressure occur, the valve will close tighter.

DETAILED DESCRIPTION OF THE INVENTION

FIGS. 1-4 illustrate, in sequence, a series of steps for producing the multiple sampling device which is the subject of the invention.

Figure 1:
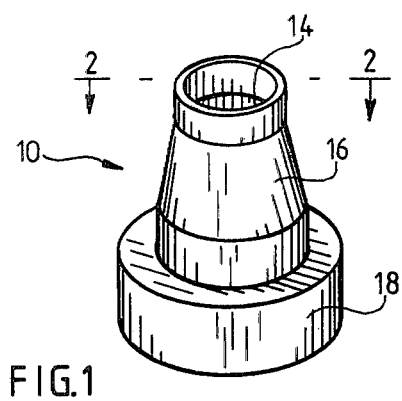
FIG. 1 is an isometric view of a sleeve valve molded to a desired shape.
Figure 2:
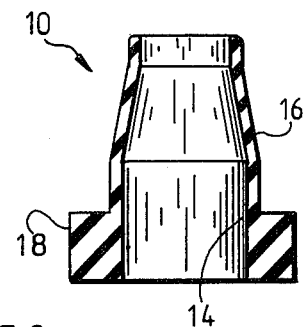
FIG. 2 is a section elevation view of the sleeve valve of FIG. 1.
Figure 3:
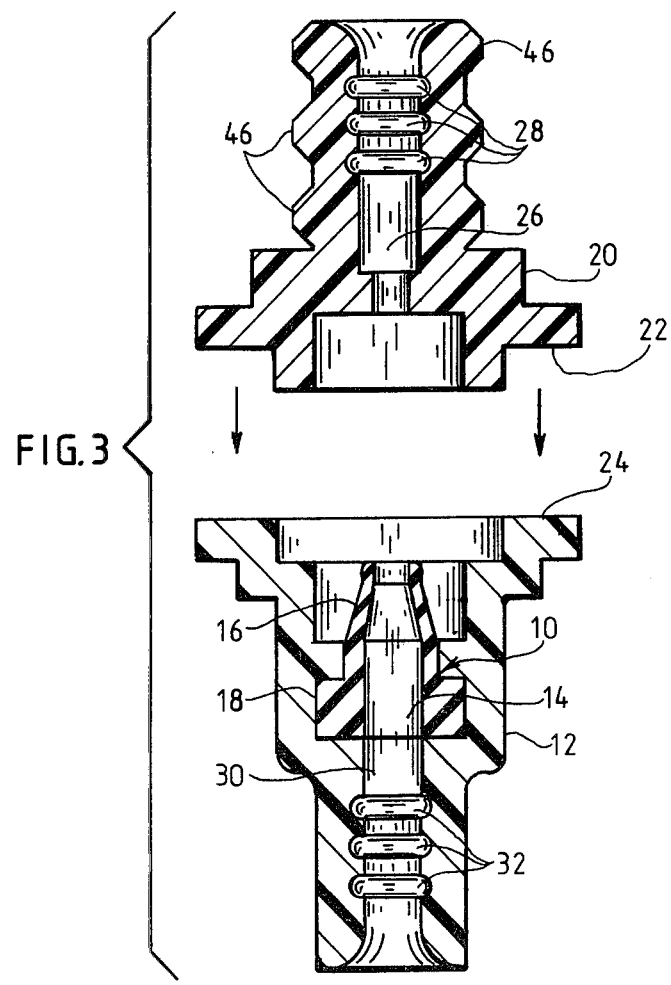
FIG. 3 is a sectional elevation view of a needle hub assembly having a valve molded therein as it is assembled to a second hub assembly.

A two material molding machine is used for molding the valve 10 and "intravenous" plastic hub 12. The valve is molded first to produce a structure as shown in FIG. 1. A thermoplastic elastomer is utilized for the valve material. The valve shown in the drawings is intended to function as a sleeve valve in a manner to be explained later. It has a generally tubular configuration with a bore 14 passing axially therethrough. One end portion thereof includes flexible conical walls 16. The other end includes an axially extending rim 18 giving the valve a hat-shaped appearance.

Once the valve is molded within an appropriately shaped cavity in the molding machine, the core with the valve on it is indexed into a second cavity. (The core is the part of the mold about which the valve is formed, and creates the bore 14 therein). The second cavity is constructed so as to give the intravenous hub 12 its desired shape. This hub is molded around the rim 18 and a portion of the conical walls. A one-piece structure is created with the encased rim preventing any possible displacement of the valve.

A second hub 20 is molded in a conventional manner. It has a surface 22 adapted to mate with the distal surface 24 of the intraveous hub. A bore 26 is provided for accomodation of a cannula. Several circumferential grooves 28 are formed in the walls defining the bore. The intravenous hub 12 is similarly formed with a bore 30 and circumferential grooves 32.

An intravenous cannula 34 is inserted within bore 30. Epoxy may be utilized within the grooves 32 to secure the cannula. Additional epoxy 36 is employed near the opening of the bore 30. A second cannula 38 having an end adapted for puncturing the stopper of an evacuated collection tube is secured within bore 26. The method of attachment is similar to that of the intravenous cannula 34.

Figure 4:
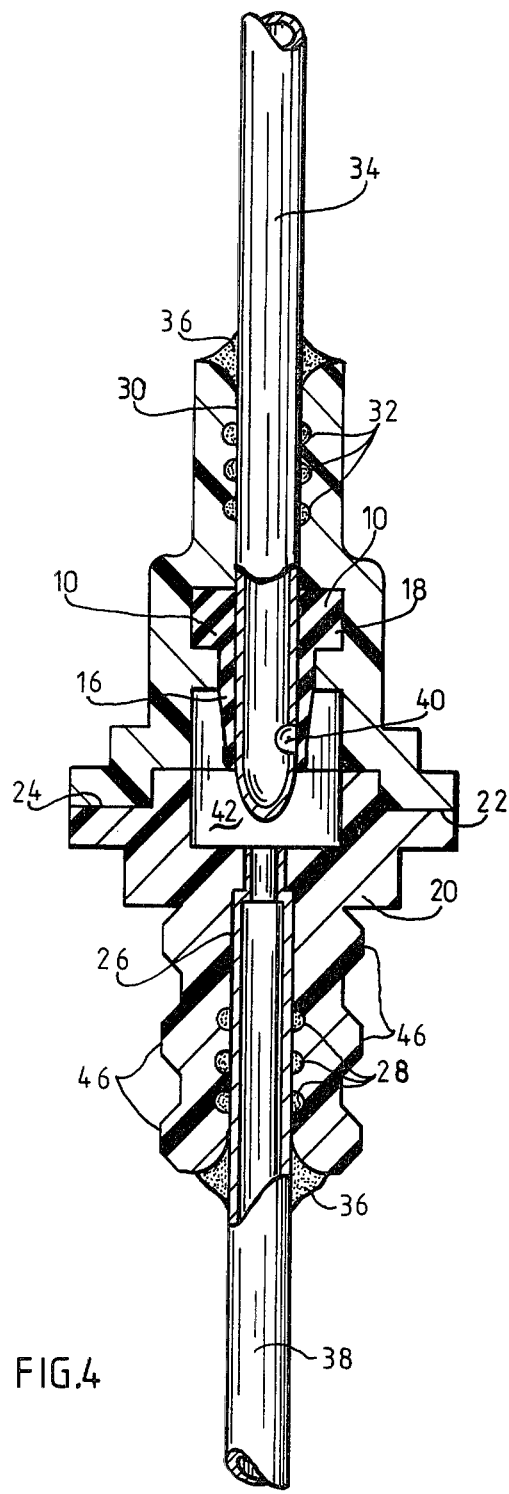
FIG. 4 is a sectional elevation view of a blood sampling apparatus after assembly of the valve, hubs, and a pair of cannulas.

The cannulas are then covered by shields (not shown), and the two hubs are permanently joined along their mating surfaces. The assembly shown in FIG. 4 is thereby created. Valve 10 occludes a slotted opening 40 in the intravenous cannula 34. A chamber 42 is created into which the slotted portion of the cannula extends. The flexible conical walls 16 also extend into the chamber so that they are free to move in and out of contact with the cannula so as to open or close the slot.

Figure 5:
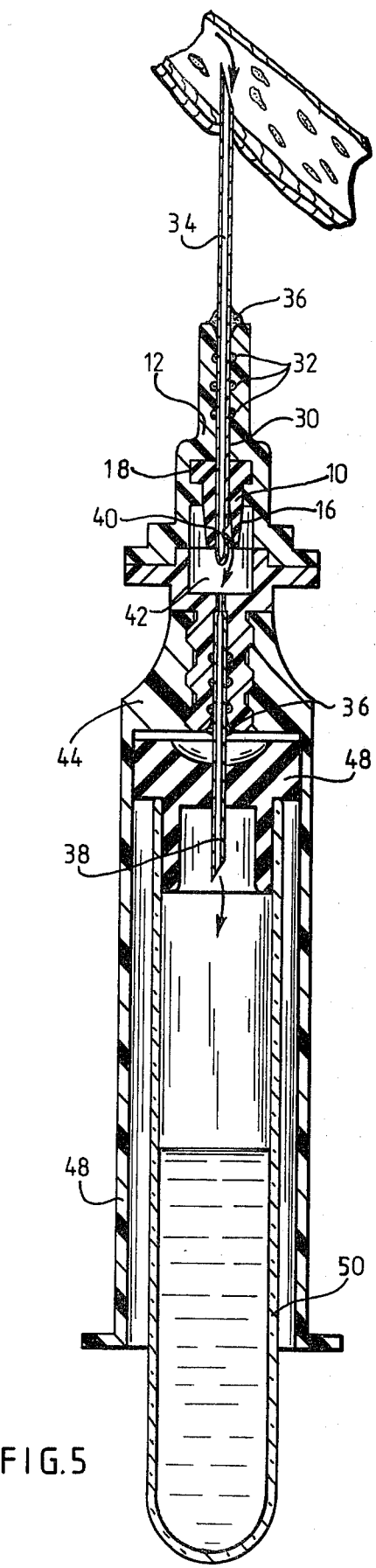
FIG. 5 is a sectional elevation of the blood sampling apparatus in use.

To use the device, a holder 44 for evacuated tubes is attached to a threaded portion 46 of the hub 20. The pointed tip of the intravenous cannula penetrates a vessel (such as a vein). The stopper 48 of an evacuated tube 50 is pierced by the tip of cannula 38. This creates a partial vacuum in the chamber 42. Due to the vacuum, the flexible walls 16 open a sufficient amount to allow blood to pass through the slot 40, into the chamber 42, and through the cannula 38 into the tube 50. FIG. 5 is illustrative of this action.

When the tube is filled and the vacuum dissipated, the resilience of the valve walls 16 causes them to reassume their normal position occluding the slot. Since the end of the hollow cannula 30 is closed, there will be no fluid communication between the cannula and the chamber.

Should back pressure occur, the valve will close tighter. The device permits multiple sampling as the same venipuncture may be used to fill a number of collection tubes without spillage. The valve prevents any flow of blood while the tubes are exchanged.

What is claimed is:

1. A multiple blood sampling device adapted to be coupled with an evacuated container to obtain blood samples from a patient, said device comprising a housing having a first hub, a second hub and chamber therein, a first cannula attached to said first hub and adapted for penetrating a blood vessel, a second cannula attached to said second hub and adapted for piercing a stopper of an evacuated collection container, and a one-way valve provided within said housing, said cannulas and said chamber being in fluid communication when said valve is in an open position, characterized in that a first portion of said valve is connected in fixed position to said first hub, and a second portion of said valve freely extends into the chamber, said second portion capable of assuming an open position to allow the passage of blood therethrough when suction is applied within the chamber by means of the second cannula, and assuming a closed position when pressures within each cannula are equal, said valve positioned inside said first hub and said chamber to be free of contact with said second hub in both open and closed conditions.

2. A device as claimed in claim 1 wherein said first cannula has an end which extends into the chamber, an opening is provided near the end of said cannula, and said second portion of the valve occludes said opening when pressures within each cannula are equal.

3. A device as claimed in claim 2 wherein said first cannula has an opening in its side and said second portion of said valve is in the form of a sleeve surrounding at least part of the end of the first cannula which extends into the chamber, including said opening.

4. A device as claimed in claim 1 or claim 3 wherein said first portion of said valve includes a circumferential rim extending outwardly therefrom, the first hub enveloping said rim to securely attach the valve to said first hub.

5. A device as claimed in claim 1 wherein said valve is made from a thermoplastic elastomer.

* * * * *